United States Patent [19]
Utley et al.

[11] Patent Number: 6,139,545
[45] Date of Patent: Oct. 31, 2000

[54] SYSTEMS AND METHODS FOR ABLATING DISCRETE MOTOR NERVE REGIONS

[75] Inventors: David Utley, San Carlos; Stuart D Edwards, Portola Valley; Richard L Goode, Los Altos, all of Calif.

[73] Assignee: VidaDerm, Sunnyvale, Calif.

[21] Appl. No.: 09/150,078

[22] Filed: Sep. 9, 1998

[51] Int. Cl.$^7$ .................................................. A61B 18/04
[52] U.S. Cl. ................................. 606/34; 607/48; 606/41
[58] Field of Search .................................. 607/48, 62, 66, 607/117, 118; 606/34, 41; 600/373, 374, 546, 548, 554, 380

[56] References Cited

U.S. PATENT DOCUMENTS

| | | |
|---|---|---|
| 4,962,766 | 10/1990 | Herzon . |
| 5,161,533 | 11/1992 | Prass et al. . |
| 5,370,642 | 12/1994 | Keller . |
| 5,505,727 | 4/1996 | Keller . |
| 5,714,468 | 2/1998 | Binder . |
| 5,800,428 | 9/1998 | Nelson et al. ............................ 606/41 |
| 5,876,336 | 3/1999 | Swanson et al. ........................ 600/374 |

*Primary Examiner*—Linda C. M. Dvorak
*Assistant Examiner*—Roy Gibson
*Attorney, Agent, or Firm*—Ryan Kromholz & Manion, S.C.

[57] ABSTRACT

Systems and method ablate motor nerve tissue by inserting an operative element connectable to an ablation energy generator into a defined percutaneous tissue region. The systems and methods apply stimulant energy in the defined percutaneous tissue region to stimulate targeted motor nerve tissue prior to ablation by the operative element. Application of the nerve ablation energy can permanently eliminate the function of a targeted motor nerve branch, to thereby inactivate a selected muscle. The muscle inactivation may, e.g., treat dystonias and other hyperfunction neuromuscular dysfunctions in the face and neck, such as torticollis, blepharospasm, and uncontrolled grimacing. The muscle inactivation may also provide cosmetic results, to eliminate or prevent aesthetically displeasing skin furrows, frowning wrinkles, or neck bands, which can arise from normal muscle contraction or prolonged exposure of the face to the sun.

22 Claims, 8 Drawing Sheets

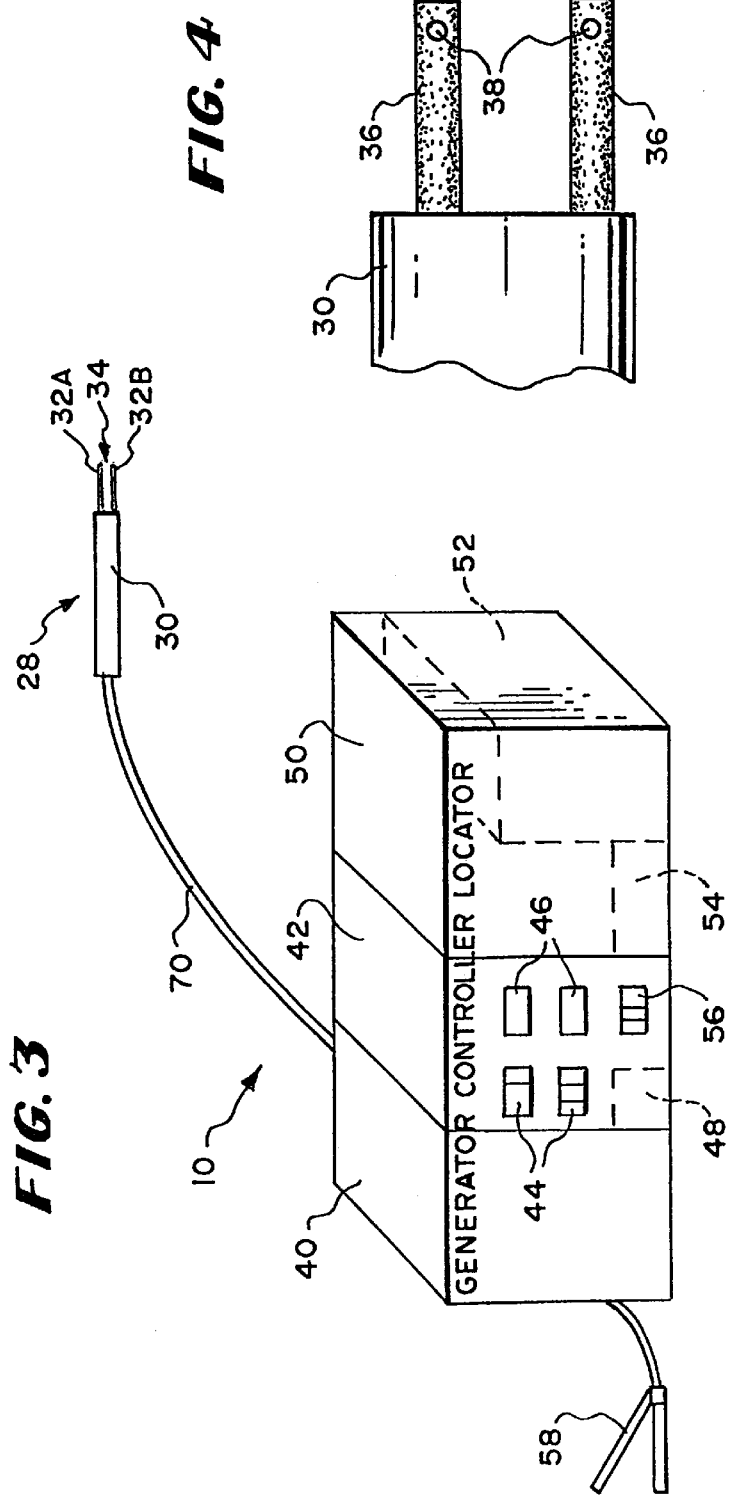

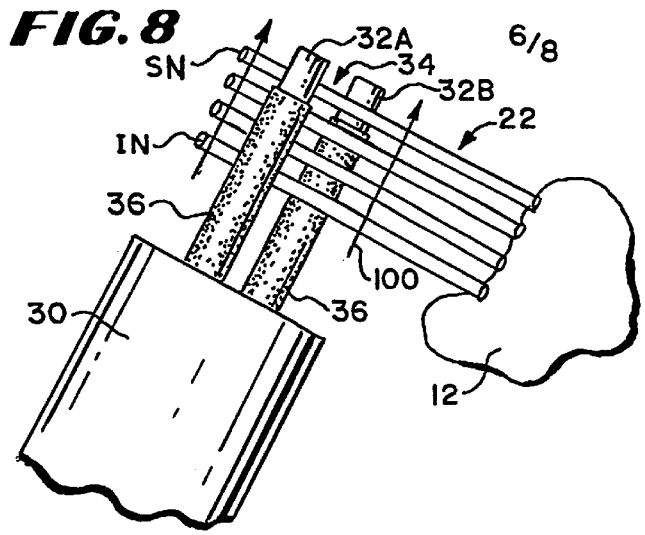
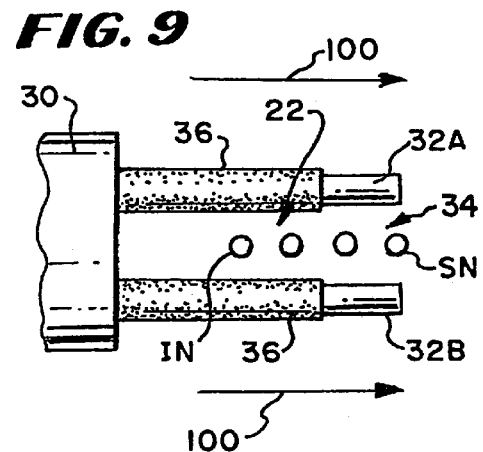
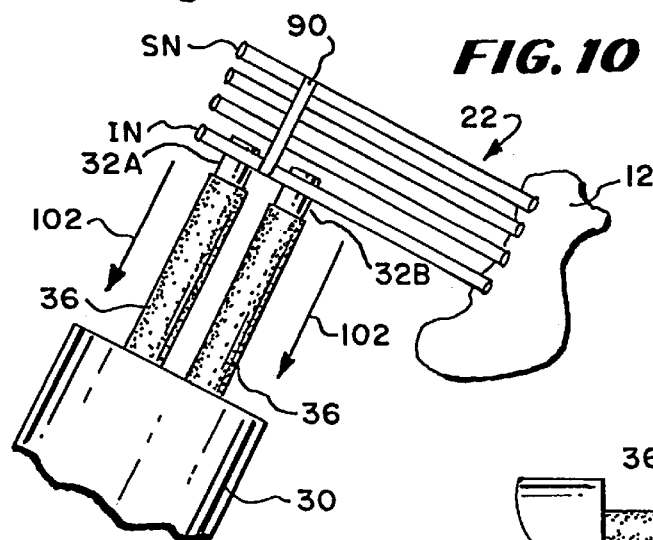
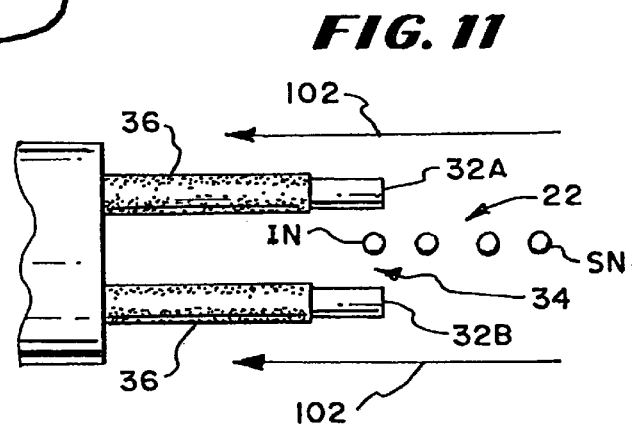
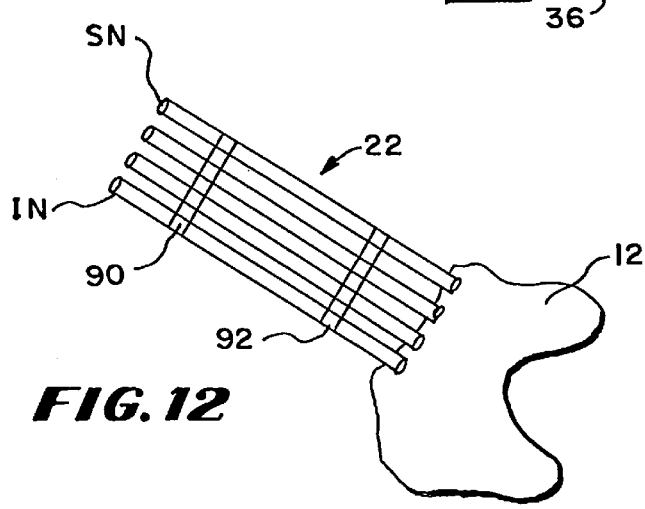

SYSTEMS AND METHODS FOR ABLATING DISCRETE MOTOR NERVE REGIONS

FIELD OF THE INVENTION

In a general sense, the invention is directed to systems and methods for treating neuromuscular hyperfunction or cosmetic conditions in the human body. In a more particular sense, the invention is directed to systems and methods for treating neuromuscular or cosmetic conditions affecting the face and neck, as evidenced either by involuntary contraction of facial or neck muscles (dystonias) or by the appearance of lines and wrinkles in the face or neck, or both.

BACKGROUND OF THE INVENTION

The human nervous system senses current information and conditions. It sends instructions to various muscles to respond. Neuromuscular disorders can disrupt this information exchange and lead to undesired muscle responses.

As one example, consider the facial and neck nerves. These motor nerves control the muscles of facial expression and, thus, an individual's outward manifestations of well being and emotion.

Dystonias, the involuntary contraction of facial or neck muscle, can distort the individual facial expressions and garble the outward appearance of an individual's feeling of well being and emotional state. For example, one type of dystonia, called blepharospasm, creates uncontrolled blinking and spasms in the eyelids. Another form of dystonia causes uncontrolled grimacing. Dystonias can also affect neck muscles, too. For example, a form of dystonia, called torticollis, causes uncontrolled contraction of the neck muscles.

Apart from these hyperfunctional disorders, normal contraction of facial and neck muscles, e.g. by frowning or squinting, can over time form permanent furrows or bands in the skin. These furrows or bands can present an aesthetically unpleasing cosmetic appearance. Exposure of the skin to the sun can accelerate this undesired wrinkling process.

As a more specific example, the facial muscle Corrugator supercilii draws the eyebrows downward and inward, producing vertical wrinkles of the forehead, also called glabellar frown lines. For this reason, Corrugator supercilii is known as the "frowning muscle" and has been called the principal agent in the expression of suffering.

Dystonias affecting the Corrugator supercilii can lead to an unfortunate, continuous frowning expression. It can also lead to the formation of hyperfunctional frown lines and wrinkles in the face, which have an adverse cosmetic effects.

A surgical forehead lift procedure is one therapeutic modality to remove glabellar frown lines. The forehead lift entails a large incision that extends from ear to ear over the top of the forehead. This surgically invasive procedure imposes the risk of bleeding and creates a large skin flap that reduces blood supply to the skin. Numbness of sensory nerves in the face, like the supraorbital nerve, can also result.

Another, less surgically invasive therapeutic modality is the administration of invertebrate exotoxins in a pharmaceutically safe form. For example, serotype A of the Botulinum toxin, when injected into the Corrugator supercilii, produces a flaccid paralysis of the muscle (see, e.g., *The New England Journal of Medicine,* 324:1186–1194. 1991). Tests have demonstrated that Botulinum toxin A may be administered into the musculature of the face without toxic effect to produce localized relation of muscle for a period of time, e.g., about six months (Blitzer, et al., *Otolaryngol Head and Neck Surg.,* 119:1018–1023, 1993).

The desired removal of hyperfunctional frowning lines is temporary. Repeated treatments are required.

In a related area, U.S. Pat. No. 5,714,468 reports the periodic injection of invertebrate neurotoxin, such as Botulinum toxin A, into facial muscles to reduce the pain associated with migraine headache.

Keller U.S. Pat. No. 5,370,642 employs laser energy to eliminate glabellar frown lines and forehead wrinkles. The laser energy causes large scale resection of the corrugator and other facial muscles to inactivate them. Like the surgical forehead lift, numbness of supraorbital nerve and other sensory nerves in the face can result.

SUMMARY OF THE INVENTION

The invention provides systems and methods of treating a given neuromuscular or cosmetic condition by selectively targeting and then inactivating a discrete motor nerve branch or branches. The systems and methods are surgically non-invasive and do not require large scale inactivation of other muscles and other nerves not causing the condition giving rise to the treatment. The invention makes possible the non-invasive selection of discrete motor nerve branches, which are small and interspersed in muscle, making them difficult to see and detect, for the purpose of specifically targeting them for ablation.

The invention provides systems and methods that ablate motor nerve tissue, e.g., one or more branches of the facial nerve, by inserting an operative element into a defined percutaneous tissue region. The operative element is connectable to a source of nerve ablation energy. The systems and methods apply stimulant energy in the defined percutaneous tissue region to stimulate targeted motor nerve tissue prior to ablation by the operative element.

In a preferred embodiment, the stimulator provides an observable positive result when targeted motor nerve tissue is in the defined tissue region. In this arrangement, the observable positive result indicates that position of the operative element should be maintained while applying ablation energy. On the other hand, the stimulator provides an observable negative result when targeted nerve tissue is not in the defined tissue region. In this arrangement, the observable negative result indicates that the operative element should be relocated before ablation energy is applied.

In a preferred embodiment, the nerve ablation energy comprises radio frequency energy. In this arrangement, the stimulant energy comprises electrical pulses, which are not radio frequency energy.

In a preferred embodiment, the stimulator is coupled to the operative element. In this arrangement, the operative element applies both ablation energy and stimulant energy.

Application of the nerve ablation energy can permanently eliminate the function of a targeted motor nerve branch, to thereby inactivate a selected muscle. The muscle inactivation may, e.g., treat dystonias and other hyperfunction neuromuscular dysfunctions in the face and neck, such as torticollis, blepharospasm, and uncontrolled grimacing. The muscle inactivation may also provide cosmetic results, to eliminate or prevent aesthetically displeasing skin furrows, frowning wrinkles, or neck bands, which can arise from normal muscle contraction or prolonged exposure of the face to the sun.

Features and advantages of the inventions are set forth in the following Description and Drawings, as well as in the appended claims.

BRIEF DESCRIPTION OF THE DRAWINGS

FIG. 3 is a perspective view of a system for treating neuromuscular conditions, which includes an operative element for both stimulation and ablating targeted nerve tissue in a defined tissue region;

FIG. 4 is an enlarged plan view of the distal end of the operative element shown in FIG. 3, which carries a bipolar electrode array;

FIG. 8 is a diagrammatic, perspective view of the bipolar electrode array shown in FIG. 4 in position to begin ablation of the nerve branches serving the Corrugator supercilii muscle;

FIG. 9 is a diagrammatic, side view of the bipolar electrode array and nerve branches shown in FIG. 8;

FIG. 10 is a diagrammatic, perspective view of the bipolar electrode array shown in FIG. 8 after having been drawn along the nerve branches serving the Corrugator supercilii muscle to form a first ablation band;

FIG. 11 is a side, diagrammatic view of the bipolar electrode array and nerve branches shown in FIG. 10;

FIG. 12 is a perspective, diagrammatic view of the nerve branches serving the Corrugator supercilii muscle after the formation of first and second ablation bands, which inactivate the muscle;

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DETAILED DESCRIPTION OF THE PREFERRED EMBODIMENTS

The invention provides systems and methods of treating neuromuscular or cosmetic conditions. The system and methods are applicable for use throughout the body. However, the systems and methods are particularly well suited for treating neuromuscular or cosmetic conditions in the facial area of the body. For this reason, the systems and methods will be described in this context.

I. NEUROMUSCULAR ANATOMY OF THE FACE

Figure 1:
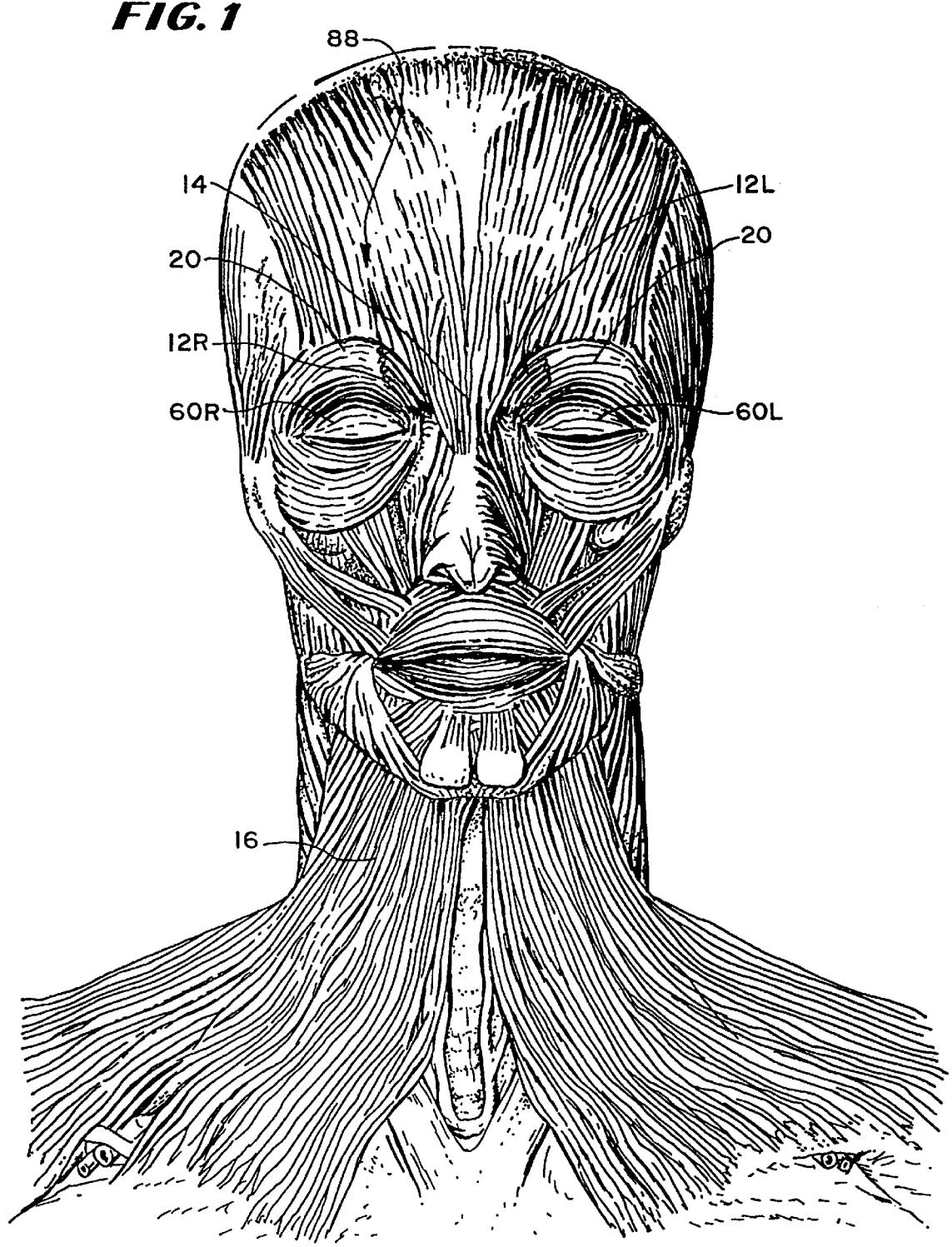
FIG. 1 is an anterior view of the face showing the superficial facial and neck muscles.

FIG. 1 shows an anterior (front) view of the principal superficial facial and neck muscles, which express human emotion. These muscles include the left and right Corrugator supercilii 12L and 12R, the Procerus 14 (also called the Pyramidalis nasi), and the Platysma myoides 16.

Figure 2:
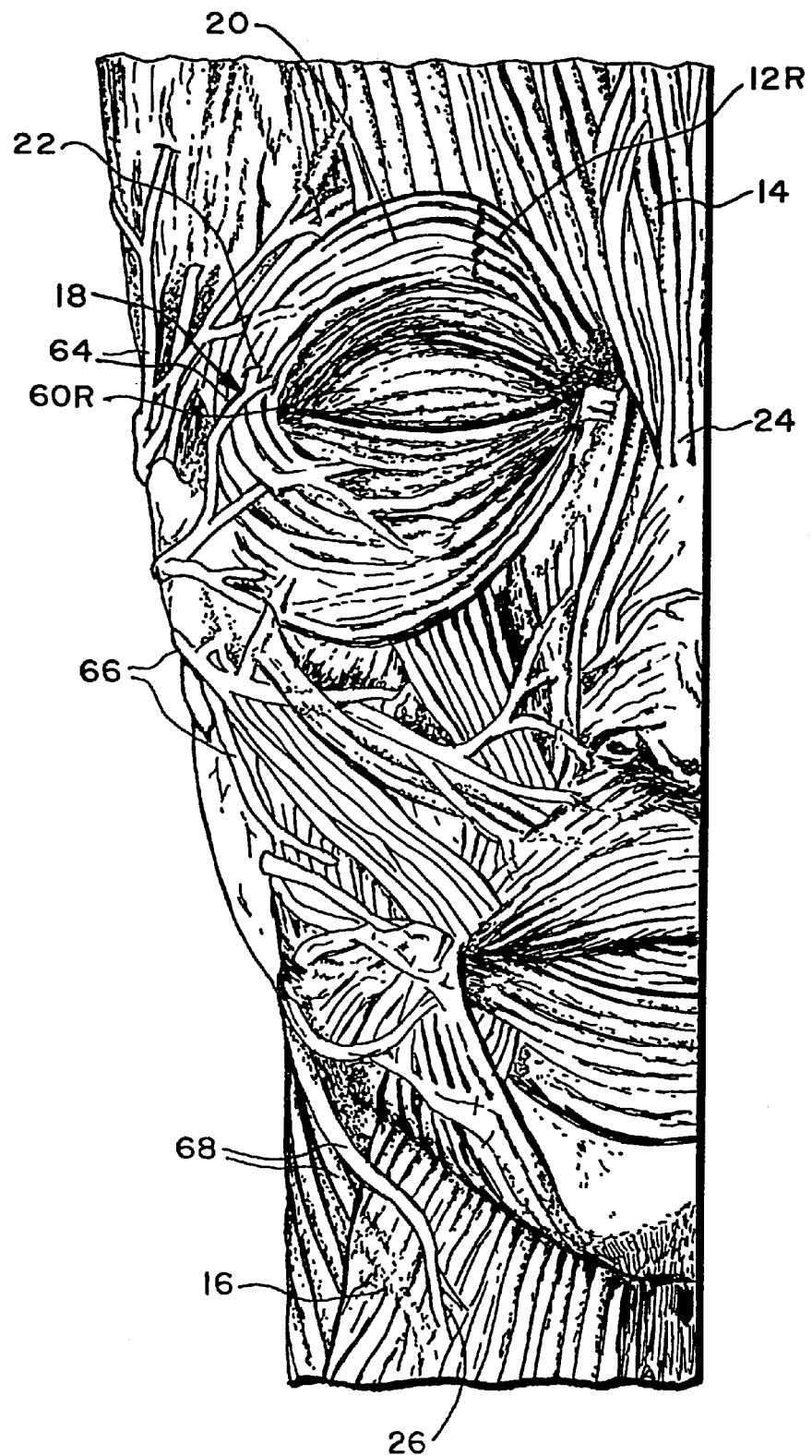
FIG. 2 an anterior view of the left side of the face, showing the superficial facial and neck muscles and the branches of the facial nerve that control them.

As FIG. 2 shows, the facial nerve 18 is the motor nerve of all the muscles of expression in the face. Its branches pass around and through superficial facial and neck muscles to control the Corrugator supercilii muscle 12, the Procerus muscle 14, and the Platysma myoides muscle 16, among many others. The facial nerve 18 is the seventh cranial nerve, which is part of the peripheral nervous system of the body.

It should be noted that the views shown in FIGS. 1 and 2 are not intended to be strictly accurate in an anatomic sense. FIGS. 1 and 2 show the facial and neck muscles and nerves in somewhat diagrammatic form to demonstrate the features of the invention.

The Corrugator supercilii 12 is a small, narrow, pyramidal muscle. As shown in FIG. 1, it is located at the inner extremity of the eyebrow beneath the Orbicularis palpebrarum muscle 20. As FIG. 2 shows, the Temporal branch 64 of the facial nerve 18 provides additional nerve branches 22 to the Corrugator supercilii muscle 12, to control the Corrugator supercilii muscle 12. The Corrugator supercilii muscle 12 is called the "frowning muscle," because it draws the eyebrows downward and inward, producing vertical wrinkles in the forehead and in the space between the eyebrows.

The Procerus 14 is a small pyramidal band of muscles (see FIG. 1) located over the nasal bone between the eyebrows. The Zygomatico-Buccal branch 66 of the facial nerve 18 (see FIG. 2) supplies the Procerus muscle 14. The Procerus muscle 14 draws down the inner angle of the eyebrows and produces transverse wrinkles over the bridge of the nose.

The Platysma myoides 16 is a broad, thin plane of muscular fibers (see FIG. 1), located immediately beneath the superficial facia on each side of the neck. The Cervical branch 68 of the facial nerve 18 (see FIG. 2) supplies the Platysma myoides muscle 16. The Platysma myoides muscle 16 produces a wrinkling of the surface of the skin of the neck, in an oblique direction, when the entire muscle is brought into action. It also serves to draw down the lower lip and angle of the mouth on each side.

Neuromuscular disorders can lead to uncontrolled contraction of one or more of these muscles 12, 14, and 16. Uncontrolled contraction of the Corrugator supercilii muscle 14 or the Procerus muscle 14 can continuously contract the brow, giving the outward appearance of displeasure or disapproval, even in the absence of the corresponding emotional state. Even without hyperfunctional dysfunction, normal contraction of these muscles can, over time, cause aesthetically displeasing frown lines or furrows in the forehead or in the space between the eyebrows. Exposure to the sun can accelerate this wrinkling process.

Likewise, uncontrolled contraction of the Platysma myoides muscle 16 (called torticollis) leads to sudden neck movement. Repeated normal contraction of the Platysma myoides muscles 16 can, over time, lead to the formation of aesthetically displeasing bands in the skin area below the neck.

II. SYSTEM FOR TREATING NEUROMUSCULAR DYSFUNCTION IN THE FACE

FIG. 3 shows a system 10 for treating neuromuscular dysfunction or cosmetic displeasing conditions of the type just described. For the purpose of illustration, the features of the system 10 will be explained in the context of treating the "frowning" condition, which is caused by contraction of the Corrugator supercilii muscle 12. The frowning condition can be due to dystonias or to normal contraction over time.

In the case of dystonias, the system 10 eliminates muscular function to mediate the hyperfunctional condition. Even in the absence of dystonias, the elimination of muscular function by the system 10 cosmetically prevents the future formation of frown furrows or stops the progression of already-formed frown furrows.

A. Electrode Device

As shown in FIGS. 3 and 4, the system 10 includes an operative device 28. In the illustrated embodiment, the device 28 includes a handle 30, made, e.g., from molded plastic. The handle 30 is sized to be conveniently grasped like a pencil by a physician.

In the illustrated embodiment, a bipolar array of spaced-apart needle electrodes 32 extend from the distal end of the handle 30. As FIG. 4 best shows, the array spaces the electrodes 32 apart, so that it creates a defined area 34 between the electrodes 32.

In the illustrated embodiment, the array comprises a pair of bipolar metallic electrodes, designated 32A and 32B, made, e.g., from stainless steel, platinum, other noble metals, or combinations thereof. In use, energy transmitted by one of the electrodes, e.g. 32A, is returned by the other electrode, e.g., 32B, to patient ground, or vice versa.

In the illustrated embodiment, the electrodes 32A and 32B are capable of being conditioned to operate in two different operational states. Operated in a first state, the electrodes 32A and 32B are conditioned to transmit a form of energy that stimulates targeted nerve tissue. Operated in the second state, the electrode 32A and 32B are conditioned to transmit a form of energy that heats and ablates the targeted nerve tissue. Alternatively, the electrodes 32A and 32B could be constructed to deliver a chemical or other substance to ablate nerve tissue.

The size and spacing of the electrodes 32A and 32B shown in FIGS. 3 and 4 are purposely set to penetrate the skin to a depth sufficient to span a targeted nerve or nerve within the defined (now percutaneous) region 34 bounded by the electrodes 32A and 32B. For the purpose of illustration, the targeted nerve or nerves lay within the branches 22 serving the Corrugator supercilii muscle 12, which extend beneath the skin under the left and right eyebrow (see FIG. 2).

When used for this purpose, the electrodes 32A and 32B each possesses a total length of about 2.5 cm. An electrical insulating material 36 surrounds the proximal end of each electrode 32A and 32B. This leaves an exposed, non-insulated length of from about 3 mm to about 10 mm. The electrodes 32A and 32B are mutually spaced apart by about 0.5 mm to 3.0 mm, which defines the bounds of the defined area 34. The ratio between exposed and insulated regions on the electrodes 32A and 32B affects the impedance of the electrodes 32A and 32B during use. Generally speaking, the larger the exposed region is compared to the insulated region, a larger impedance value can be expected.

The size and spacing of the electrodes 32A and 32B for use in association with a different nerve branch, can be ascertained by medical professionals using textbooks of human anatomy along with their knowledge of the site and its disease or injury.

In the illustrated embodiment (see FIG. 4), at least one electrode 32A and 32B carries a temperature sensing element 38. In a bipolar arrangement, at least the electrode which transmits the energy should a temperature sensing element 38. In the illustrated embodiment, each electrode 32A and 32B carries one or more temperature sensing elements 38. The elements 38, in use, sense local temperature conditions to provide information used to control the ablation process, as will be described later. In the illustrated embodiment, each element 38 comprises a thermocouple, which is carried at the tip of each needle electrode 32A and 32B (which senses temperature conditions in the region where the energy is transmitted) as well as within the proximal insulation 36 (which senses temperature conditions in a region remote to where the energy is transmitted).

Figure 5:
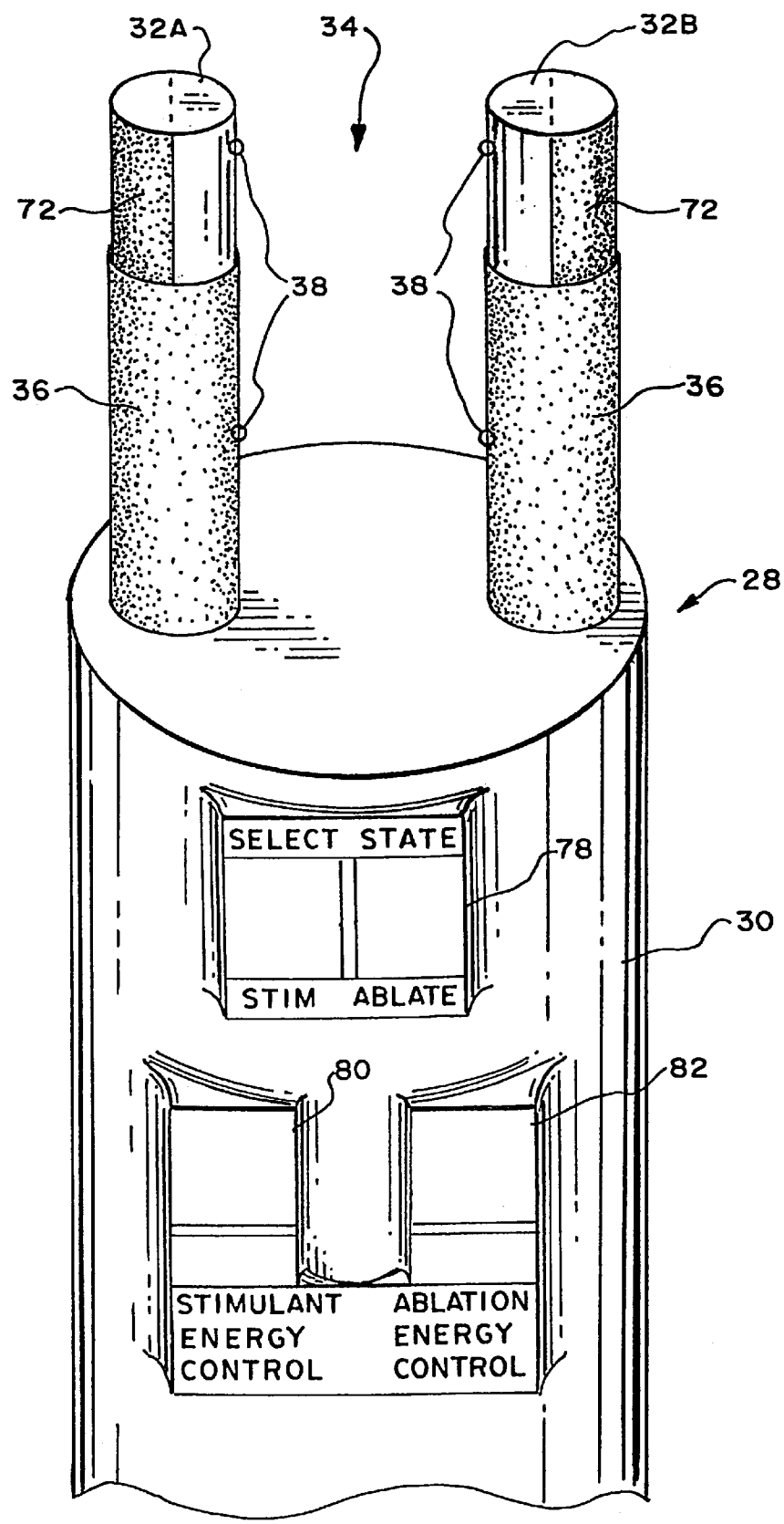
FIG. 5 is an enlarged perspective view of an alternative embodiment of the operative element and bipolar electrode array shown in FIG. 4, in which the backsides of the electrodes are coated with an electrical insulating material, and in which the handle carries various energy control switches coupled to the system shown in FIG. 3.

In shown in FIG. 5, the backside of each energy transmitting region of the electrodes 32A and 32B, which faces away from the defined area 34, can also carry electrical insulating material 72. The material 72 serves to additionally focus the transmission of energy into the defined area 34.

Figure 6:
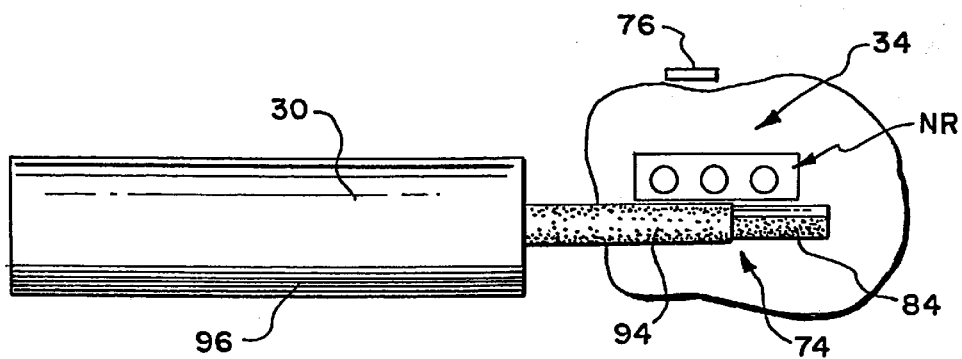
FIG. 6 is a side view of an alternative embodiment of the operative element for use with the system shown in FIG. 3, in which the operative element carries a unipolar electrode.

As FIG. 6 shows, the handle 30 could carry a unipolar electrode array 74, comprising e.g., a single metallic electrode. In use, energy transmitted by the electrode 74 is returned by an external patch 76 electrode on the patient's skin, which is coupled to ground. An electrical insulating material 94 covers the proximal portion of the electrode 74, the same manner as the material 36 on the electrodes 32A and 32B. This leaves the distal region of the electrode 74 exposed for the transmission of energy.

In this arrangement, as shown in FIG. 6, the defined area 34 includes the nerve tissue region (designed NR in FIG. 6), which lays in the electrical path between the transmitting electrode 74 and the patch electrode 76. As FIG. 6, half of the electrode 74 can carry an electrical insulating material 84, to further direct transmitted energy toward the defined area 34. In this arrangement, the handle 30 includes an indicator band 96, which aligned with the insulating material 84. The indicator band 96 allows the physician to visually ascertain the orientation of the electrode 74 without actually viewing it.

The use of a bipolar array 32A and 32B as shown in FIGS. 3 and 4 is preferred, because it facilitates the targeted delivery of energy to the defined area 34. Still, a unipolar electrode array 74 like that shown in FIG. 6 can be constructed and oriented with respect to the exterior patch electrode 76, to achieve a targeted delivery of energy to the defined area 34, with an efficacious result comparable to a unipolar electrode array.

B. Ablation Energy Generator

As FIG. 3 also shows, the system 10 also includes an energy generator 40. In the illustrated embodiment, the generator 40 generates radio frequency energy (e.g., having a frequency in the range of about 400 kHz to about 10 MHZ).

A controller 42 is coupled to the radio frequency generator 40. The controller 42 assures that the radio frequency energy is supplied at power levels appropriate to achieve the desired treatment. In the case of nerve ablation, the controller 42 supplies radio frequency energy at a power level of about 1 W to 15 W, to ohmically heat nerve tissue to temperatures of about 85° C., where ablation of nerve tissue occurs.

A control cable 70 carried by the handle 30 is coupled to controller 42 and generator 40. The control cable 70 conveys radio frequency energy from the generator 40 to the electrodes 32A and 32B. The cable 70 also conveys sensed temperature conditions from the electrodes 32A and 32B to the controller 42.

The controller 42 includes an operator input 44. The input 44 can comprise, e.g., an array of manually operated control buttons and switches. In the illustrated embodiment, the input 44 includes a setting to input a desired temperature condition sensed at each thermocouple (in ° C.); a desired maximum power output (in Watts); and a desired maximum impedence condition sensed between the electrodes 32A and 32B (in ohms). Alternatively, the maximum impedance condition can be preset at a desired control value, e.g., 1000 ohms.

In the illustrated embodiment (see FIG. 3), the controller 42 also includes an output device 46. The output device 46 can comprise,. e.g., a digital LED display or analog display. The output 46 displays current operating conditions.

Before beginning a procedure, the controller 42 receives desired ablation control parameters from the physician through the input device 44. The controller 42 includes a preestablished control algorithm 48, which processes actual conditions in comparison to the desired conditions, such as local temperature conditions supplied by the sensors 38, tissue impedance sensed between the electrodes 32A and 32B, and the power level of the generator 40. Using the algorithm 48, the controller 42 governs the power level of the generator 40 in response to these inputs to supply radio frequency energy to the electrodes 32A and 32B to meet the desired control criteria for ablation.

In the illustrated embodiment, the controller conditions the electrodes 32A and 32B to operate in a bi-polar mode. That means that the radio frequency energy transmitted by one of the electrodes, e.g. 32A, is returned by the other electrode, e.g., 32B, to patient ground, or vice versa.

C. Targeted Nerve Detection Module

The system 10 (see FIG. 3) further includes a module 50 coupled to the controller 42. The module 50 determines whether the targeted nerve tissue region lies between the region 34 defined between electrodes 32A and 32B, where ablation energy is to be delivered. The module 50 provides a result indicative of the presence (or absence) of the targeted nerve tissue region within the ablation energy delivery zone (i.e., the defined region 34). The result is observable by the physician to position the electrodes 32A and 32B to best target the ablation energy to the desired nerve tissue region.

The module 50 includes a nerve tissue stimulator 52. The stimulator 50 can comprise a separate module coupled to the controller 42. Alternatively, the stimulator 50 can be an integrated part of a single unit, which houses the generator 40, controller 42, and stimulator 50.

The purpose of the stimulator 52 is to apply stimulant energy to the targeted nerve region capable of invoking an observable physiological response, without ohmically heating the targeted nerve region. Nerve tissue is, generally speaking, highly sensitivity to electrical stimulation. Thus, low frequency DC energy pulses (0.5 to 3 Hz) can be applied at low current levels (e.g., from about 0.5 mA to about 1.0 mA) for this purpose, with no ohmic heating effects. The stimulant energy can be applied as DC square pulses, having a pulse width of no more than about 200 msec.

In the illustrated embodiment, the stimulator 52 comprises an electrical pulse generator. To direct the stimulant energy into the defined region 34, bi-polar transmission is applied. That is, one electrode 32A serves as the pulse transmitting electrode, while the other electrode 32B serves as the return path.

In the illustrated embodiment, the stimulation of the branches 22 serving the Corrugator supercilii muscle 12 by low current electrical DC pulses, as described, leads to a noticeable, periodic contraction of the associated left or right Corrugator supercilii muscle 12, with a resultant twitching of the respective eyebrow.

The module 50 includes a response observer 54. The observer 54 watches physiologic results (or lack of results) in response to the stimulant energy. In the illustrated embodiment, the observer 54 watches the movement of the left or right eyebrow, while the stimulator 52 supplies the selected stimulant energy to the defined region 34.

The observer 54 can take various forms. Movement of either eyebrow can be either visually observed by the physician or an assistant, in which case the physician or assistant comprise the observer 54. Movement of either eyebrow can also be observed by electrical monitoring using, e.g., an electromyogram, which, in this instance, comprise the observer 54.

If the targeted nerve region lies within the defined ablation energy delivery zone 34 between the electrodes 32A and 32B, the stimulant energy supplied by the stimulator 52, which is also transmitted between the electrodes 32A and 32B into the zone 34, will evoke a strong contraction of the associated Corrugator supercilii muscle 12. A strong twitch of the corresponding eyebrow will be observed.

Likewise, if the targeted nerve region lies outside the ablation energy delivery zone 34, the stimulant energy supplied by the stimulator 52, which is transmitted between the electrodes 32A and 32B, will not evoke a contraction of the associated Corrugator supercilii muscle 12. No eyebrow twitch will be observed.

A positive response (repeated eyebrow twitching) can be easily distinguished from a negative response (no eyebrow twitching). The presence of a negative response to the stimulant energy indicates that the electrodes 32A and 32B should be relocated to span the targeted nerve tissue. The presence of a positive response indicates that the targeted nerve tissue is positioned within the defined tissue region 34 between the electrodes 32A and 32B.

In this way, the module 50 aids the physician in finding and confining the targeted nerve within the zone 34 targeted for ablation.

The system 10 includes an operational state selection switch 56. The switch 56 can be toggled between a first operation state and a second operational state. In the first state, the stimulation module 50 is actuated. In the second state, the generator 40, and the associated controller 42, are actuated.

In FIG. 3, the state selection switch 56 is located on the front panel of the controller 42. Alternatively, as shown in FIG. 5, a state selection switch 78 can be mounted on the handle 30 of the device 28. In this arrangement, the physician can switch operational states by thumb control of the switch 78, without need to touch the controller 42.

In FIG. 3, the system 10 also includes a foot switch 58. The physician can depress or relieve the foot switch 58, to turn the selected operational state on and off, respectively.

Alternatively (as FIG. 5 shows), the handle 30 can carry a stimulant energy control switch 80, which the physician can operate by thumb control to transmit stimulant energy, while using the foot switch 58 to control the application of radio frequency energy. In another alternative arrangement (as FIG. 5 also shows), the handle 30 can carry the state selection switch 56, a stimulant energy control switch 80, and a radio frequency energy control switch 82.

II. USE OF THE SYSTEM FOR TREATING NEUROMUSCULAR DYSFUNCTION IN THE FACE

FIGS. 7 to 12 show the use the system 10 to treat dysfunction of the Corrugator supercilii muscle 12.

Figure 7:
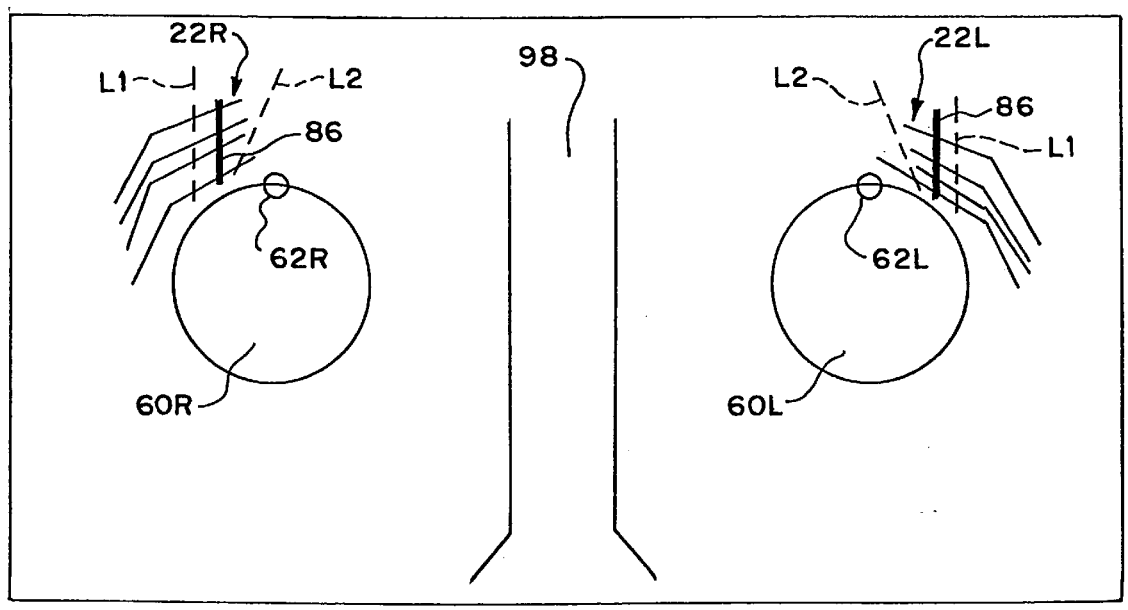
FIG. 7 is a diagrammatic view of the eye region of a human face, showing the regions in which the operative device shown in FIG. 4 is inserted for the purpose of ablating the nerve branches serving the Corrugator supercilii muscle.

As FIG. 7 shows, the physician first externally locates and marks the anatomic region where the nerve branches 22 supplying the Corrugator supercilii muscle 12 lay. This region can be ascertained by medical professionals using textbooks of human anatomy along with their knowledge of the site and its disease or injury.

Generally speaking (see FIG. 7), the region of the right nerve branches 22R for the right Corrugator supercilii muscle is identified by scribing a vertical mark 86 on the skin of the patient. To scribe the mark 86, the physician tactilely locates the right supraorbital sensory nerve 62R, which lays in a groove centrally above the right eye socket 60R. The physician measures laterally (i.e., away the bridge 98 of the nose) 1.0 cm and there scribes a vertical mark 86, which extends 1.6 cm upward from the rim of the eye socket 60R. The same relative measurement technique can be used to mark the location of the left nerve branches 22L over the left eye socket 60L.

Before inserting the electrodes 32A and 32B, the physician establishes a regional block. For example, the physician can inject lidocaine into the supraorbital nerve 62 of the selected region.

Aided by the mark 86, the physician inserts the electrodes 32A and 32B into the selected region, from inferior to superior, through the eyelid and brow. The electrodes 32A and 32B are inserted in a generally vertical orientation spaced from the muscle, as shown by dotted line L1 in FIG. 7.

The physician selects operation of the stimulation module using the switch 56 (or switch 78 on the handle 30). Depressing the foot switch 58 (or, alternatively, operating the control switch 80 on the handle 30), the physician sends stimulation energy between the electrodes 32A and 32B, as deployed in the selected region.

If the observer 54 indicates a negative response (i.e., no twitching of the associated left or right Corrugator supercilii muscle), the physician interrupts the stimulation energy (using the foot switch 58 or handle switch 80) and relocates the electrodes 32A and 32B in another vertical orientation line L1 above the eye socket. Once relocated, the physician again sends stimulation energy between the electrodes 32A and 32B. These steps are repeated in the selected region, until the observer 54 indicates a positive response, i.e., twitching of the associated Corrugator supercilii muscle.

Once the positive response is observed, the physician manipulates the electrodes 32A and 32B to place the targeted nerve branches 22 as a group between the electrodes 32A and 32B, as FIGS. 8 and 9 illustrate. Applying the stimulant energy, the physician slowly advances the electrodes 32A and 32B from inferior to superior, as shown by arrows 100 in FIGS. 8 and 9, while observing a consistent positive response from the Corrugator supercilii muscle. This indicates that the electrodes 32A and 32B span the targeted nerve branches 22, in the manner shown in FIGS. 8 and 9.

Proceeding in the superior direction while applying stimulant energy, the physician will in time observe twitching of the frontalis muscle 88 (see FIG. 1) and not the Corrugator supercilii muscle 12. The indicates that the physician has advanced the distal end of the electrodes 32A and 32B beyond the most superior of the targeted nerve branches 22 (designated SN in FIGS. 8 and 9).

At this indication, the physician slowly draws the electrodes 32A and 32B backward, from superior to inferior (i.e., away from the frontalis muscle), while continuing to supply stimulant energy. When only twitching of the Corrugator supercilii muscle 12 is next observed, the physician knows that the distal end of the electrodes 32A and 32B are aligned with most superior nerve branch SN. This is where the physician should begin the ablation process.

Without altering the location of the electrodes 32A and 32B, the physician selects operation of the generator 40 and controller 42, using the switch 56 (or handle switch 78). Depressing the foot switch 58 (or, alternatively, operating the control switch 82 on the handle 30), the physician applies radio frequency energy to the selected region between the electrodes 32A and 32.

The controller 42 governs the operation of the generator 40 to ablate the nerve branches 22 which lay in the defined area 34 between the electrodes 32A and 32B. According to operating conditions prescribed by the input 44, and based upon temperature conditions sensed by the thermocouples 38, the controller 42 applies radio frequency energy.

For example, the controller 42 can supply the ablation energy at between about 2 W to 10 W, to maintain a target temperature of about 85° C., until tissue impedance in excess of about 1000 ohms is sensed. Total Joules delivered will vary between about 20 J to 200 J according to the exposed length of the electrodes 32A and 32B.

During the nerve ablation process, the insulation material 36 on the proximal ends of the electrodes 32A and 32B, protects tissue surrounding the targeted nerve region from ohmic heating and damage. This further serves to focus the ohmic heating effect in the defined area 34.

If the exposed lengths of the electrodes 32A and 32B, which extend beyond the insulation sleeve 36, span the entire targeted nerve branch region 22, a single application of energy without movement of the electrodes 32A and 32B will provide the desired ablation result. However, when the exposed lengths of the electrodes 32A and 32B span only a portion of the targeted nerve branches 22 (as in FIGS. 8 and 9), the electrodes 32A and 32B must be moved across the nerve branches 22 to successively expose all nerve branches 22 to ablation energy.

More particularly, as FIGS. 10 and 11 show, while radio frequency energy is applied, the physician draws the electrodes 32A and 32B (as shown by arrows 102 in FIGS. 10 and 11) slowly from the most superior nerve branch SN toward the most inferior nerve branch (designated IN in FIGS. 10 to 11). The slow pace of electrode travel maintains the desired ablation temperature condition within the defined area 34. The physician continues to draw the electrodes 32A and 32B along this path, until the non-insulated sleeves 36 of the electrodes 32A and 32B are nearly withdrawn from the skin. At this time, the physician terminates the application of radio frequency energy.

In this way, the physician exposes each nerve branch 22 in succession to the ablating effect of the radio frequency energy within the defined area 34. A proximal ablation band 90 (see FIGS. 10 and 12) is formed.

The physician next angles the electrodes 32A and 32B in a medial direction (i.e., toward from the bridge 98 of the nose) toward the muscle 12. The physician inserts the electrodes 32A and 32B along an orientation line L2, which lays closed to the Corrugator supercilii muscle than the first orientation line L1. The physician transmits stimulant energy to locate and span the nerve branches 22 in this more distal region of the nerve branches 22.

While transmitting stimulant energy, the physician repeats the sequence of steps just described, to position the defined area 34 so that it bridges the most superior nerve branch SN in the more distal region. The physician then applies the radio frequency energy, while drawing the electrodes 32A and 32B slowly from the most superior nerve branch SN to the most inferior nerve branch IN. When the non-insulated sections of the electrodes 32A and 32B are nearly withdrawn from the skin, the physician terminates the application of radio frequency energy.

In this way, the physician again exposes each nerve branch in succession to the ablating effect of the radio frequency energy with the defined area 34, forming a second, more distal ablation band 92 spaced from the first band 90(see FIGS. 7 and 12).

The ablation of the motor nerve branches 22 inactivates the associated Corrugator supercilii muscle. The establishment of a proximal ablation band 90 and a distal ablation band 92 effectively assures that nerve paths will not reform after ablation.

The physician can, if desired, confirm the desired inactivation of the Corrugator supercilii muscle. To accomplish this, the physician reinserts the electrodes 32A and 32B in the nerve branch region between the ablation bands 90 and 92 and applies stimulant energy. The consistent lack of a positive response while the electrodes 32A and 32B roam the nerve region confirm that the ablation has achieved the desired inactivation of the Corrugator supercilii muscle.

With the termination of the ablation cycle, the physician removes the electrodes 32A and 32B. The physician applies ice to the skin over the treated region, to mediate swelling. The physician repeats the above-listed treatment steps to the nerve branches on the opposite side of the face.

Once the treatment is concluded, the patient is free to resume regular activity.

The ablation of a defined motor nerve region permanently eliminates function of the Corrugator supercilii muscle 12. In like manner, the system 10 can be operated to locate and ablate other motor nerve regions to permanently eliminate the function of other muscles, e.g., the Procerus muscle 14 or Platysma myoides muscle 16, or other muscles. Each targeted muscle and nerve group will, of course, require its own anatomic approach and procedure, which medical professionals can ascertain using textbooks of human anatomy along with their knowledge of the site and its disease or injury.

EXAMPLE 1

Figure 13:
FIGS. 13 and 14 are, respectively, pre-operative and post-operative photographs of an individual, whose nerve branches serving the Corrugator supercilii muscle have been ablated in the manner shown in FIGS. 8 to 12 to inactivate the muscle, demonstrating the benefits of the invention.
Figure 14:

FIG. 13 shows a pre-operative view of a 37 year old female having extensive sun exposure, with a resulting aesthetically displeasing frowning condition. A bipolar group of electrodes as shown in FIGS. 3 and 4 were inserted and operated in the manner just described to locate the motor nerve branches supplying the Corrugator supercilii muscle. Once located, the motor nerve branches were ablated by applying radio frequency energy at 4 W (maximum), impedance 800 ohms, for twenty seconds. Left and right side ablations were performed in this manner, with proximal and distal ablation bands on each side. No complications were experienced. FIG. 14 shows a post-operative view of the patient several weeks after treatment, showing the inactivation of frowning muscle activity.

EXAMPLE 2

Figure 15:
FIGS. 15 and 16 are, respectively, pre-operative and post-operative photographs of another individual, whose nerve branches serving the Corrugator supercilii muscle have been ablated in the manner shown in FIGS. 8 to 12 to inactivate the muscle, demonstrating the benefits of the invention.
Figure 16:

FIG. 15 shows a preoperative view of a 60 year old female having extensive sun exposure, with a resulting aesthetically displeasing frowning condition. A bipolar group of electrodes as shown in FIGS. 3 and 4 were inserted and operated in the manner just described to locate the motor nerve branches supplying the Corrugator supercilii muscle. Once located, the motor nerve branches were ablated by applying radio frequency energy at 4 W (maximum), impedance 800 ohms, for twenty seconds. Left and right side ablations were performed in this manner, with proximal and distal ablation bands on each side. No complications were experienced. FIG. 16 shows a post operative view of the patient several weeks after treatment, showing the inactivation of frowning muscle activity. The patient reports that her eyes are more relaxed, and the patient has a more youthful appearance.

Various features of the invention are set forth in the following claims.

We claim:

1. A motor nerve tissue ablation system comprising an operative element connectable to an ablation energy generator and adapted to apply ablating energy in a defined percutaneous tissue region to ablate targeted motor nerve tissue, the operative element including at least two spaced apart bi-polar needle electrodes spanning between them the defined tissue region, and a stimulator to apply stimulant energy in the defined percutaneous tissue region to stimulate targeted motor nerve tissue prior to ablation by the operative element.

2. A system according to claim 1 wherein the stimulator is coupled to the operative element and the stimulant energy is applied through the operative element.

3. A system according to claim 1 wherein the stimulant energy comprises an electrical pulse.

4. A system according to claim 1 wherein the generator comprises a source of radio frequency energy.

5. A system according to claim 4 wherein the stimulant energy is not radio frequency energy.

6. A system according to claim 4 wherein the stimulator is coupled to the operative element to apply the stimulant energy through the operative element.

7. A system according to claim 4 wherein the stimulant energy comprises electrical energy.

8. A facial nerve ablation system comprising an operative element connectable to an ablation energy generator and adapted to apply ablating energy in a defined percutaneous tissue region to ablate a targeted facial nerve branch, the operative element includes at least two spaced apart bi-polar needle electrodes spanning between them the defined percutaneous tissue region, and a stimulator to apply stimulant energy in the defined percutaneous tissue region to stimulate the targeted facial nerve branch prior to ablation by the operative element.

9. A system according to claim 8 wherein the stimulator is coupled to the operative element and the stimulant energy is applied through the operative element.

10. A system according to claim 8 wherein the stimulant energy comprises an electrical pulse.

11. A system according to claim 8 wherein the generator comprises a source of radio frequency energy.

12. A system according to claim 11 wherein the stimulant energy is not radio frequency energy.

13. A system according to claim 11 wherein the stimulator is coupled to the operative element to apply the stimulant energy through the operative element.

14. A system according to claim 11 wherein the stimulant energy comprises electrical energy.

15. A method for ablating motor nerve tissue comprising the steps of inserting an operative element connectable to an ablation energy generator into a defined percutaneous tissue region to ablate targeted motor nerve tissue, and applying stimulant energy in the defined percutaneous tissue region to stimulate targeted motor nerve tissue prior to ablation by the operative element.

16. A method for ablating a facial nerve branch comprising the steps of inserting an operative element connectable to an ablation energy generator into a defined percutaneous tissue region to ablate targeted facial nerve branch, and applying stimulant energy in the defined percutaneous tissue region to stimulate the targeted facial nerve branch prior to ablation by the operative element.

17. A method for ablating targeted motor nerve tissue comprising the steps of inserting an operative element into a defined percutaneous tissue region, applying to the defined percutaneous tissue region stimulant energy to affect targeted motor nerve tissue, observing a positive result when targeted motor nerve tissue is present in the defined percutaneous tissue region and a negative result when targeted motor nerve tissue is not present in the defined percutaneous tissue region, and when the positive result is observed, applying ablating energy through the operative element to ablate targeted motor nerve tissue.

18. A method for ablating a targeted facial nerve branch comprising the steps of inserting an operative element into a defined percutaneous tissue region, applying to the defined percutaneous tissue region stimulant energy to affect the targeted facial nerve branch, observing a positive result when targeted facial nerve branch is present in the defined percutaneous tissue region and a negative result when targeted facial nerve branch is not present in the defined percutaneous tissue region, and when the positive result is observed, applying ablating energy through the operative element to ablate the targeted facial nerve branch.

19. A method according to claim 17 or 18 and further including the step of changing location of the operative element when the negative result is observed.

20. A method according to claim 17 or 18 wherein the stimulant energy is applied through the operative element.

21. A method according to claim 17 or 18 wherein the ablation energy is radio frequency energy.

22. A method according to claim 21 wherein the stimulant energy is an electrical pulse.

* * * * *